US011446106B2

(12) United States Patent
Ritchey et al.

(10) Patent No.: US 11,446,106 B2
(45) Date of Patent: Sep. 20, 2022

(54) MEDICAL IMPLANT DELIVERY SYSTEM AND METHOD AND AN IMPLANT HAVING A DETACHABLE MARKING SECTION

(71) Applicant: Smith & Nephew, Inc., Memphis, TN (US)

(72) Inventors: Nicholas Ritchey, Collierville, TN (US); Kevin Belew, Hernando, MS (US); Phillip Frederick, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 17/494,222

(22) Filed: Oct. 5, 2021

(65) Prior Publication Data

US 2022/0022992 A1    Jan. 27, 2022

Related U.S. Application Data

(60) Continuation of application No. 16/421,739, filed on May 24, 2019, now Pat. No. 11,160,628, which is a
(Continued)

(51) Int. Cl.
*A61B 50/22* (2016.01)
*A61B 50/20* (2016.01)
(Continued)

(52) U.S. Cl.
CPC ............ *A61B 50/22* (2016.02); *A61B 17/865* (2013.01); *A61B 50/20* (2016.02); *A61B 50/30* (2016.02);
(Continued)

(58) Field of Classification Search
CPC ......... A61B 50/22; A61B 50/20; A61B 50/30; A61B 50/33; A61B 90/94; A61B 17/865; A61J 1/00; B65B 55/02
(Continued)

(56) References Cited

U.S. PATENT DOCUMENTS 2,333,715 A   11/1943   Hahnemann
2,405,369 A    8/1946   Poulsen
(Continued)

FOREIGN PATENT DOCUMENTS

DE    202010007487 U1   9/2010
DE    102009052838 A1   5/2011
(Continued)

OTHER PUBLICATIONS

Communication pursuant to Rule 164(2)(b) and Article 94(3) EPC, for Application No. 14799939.5, dated Mar. 11, 2020, 10 pages.
(Continued)

*Primary Examiner* — Jacob K Ackun
(74) *Attorney, Agent, or Firm* — KDB Firm PLLC

(57) ABSTRACT

Embodiments of the invention are directed to a caddy configured to receive medical implants coupled to respective holders. The medical implants and holders may be oriented and/or located in the caddy based on one or more of size, shape, and other configuration of the medical implants and holders and the openings in the caddy through which the medical implants are received. Another embodiment of the invention incudes a medical implant having an implant body portion and a detachable marking portion that is connected to the implant body portion by a frangible region structured to provide selective separation of the implant body portion from the detachable marking portion upon application of a force or torque to the implant body portion, and the detachable marking portion including one or more markings that correspond to identifying information associated with features or characteristics of the implant body portion.

20 Claims, 13 Drawing Sheets

Related U.S. Application Data division of application No. 15/033,482, filed as application No. PCT/US2014/063417 on Oct. 31, 2014, now abandoned.

(60) Provisional application No. 61/919,154, filed on Dec. 20, 2013, provisional application No. 61/898,531, filed on Nov. 1, 2013.

(51) Int. Cl.
| | |
|---|---|
| *A61B 50/30* | (2016.01) |
| *A61B 50/33* | (2016.01) |
| *A61B 90/94* | (2016.01) |
| *A61B 17/86* | (2006.01) |
| *A61J 1/00* | (2006.01) |
| *B65B 55/02* | (2006.01) |

(52) U.S. Cl.
CPC .............. *A61B 50/33* (2016.02); *A61B 90/94* (2016.02); *A61J 1/00* (2013.01); *B65B 55/02* (2013.01)

(58) Field of Classification Search
USPC ................................................ 206/370, 438
See application file for complete search history.

(56) References Cited

U.S. PATENT DOCUMENTS

| | | |
|---|---|---|
| 4,199,057 A | 4/1980 | Gruaz |
| 4,762,688 A | 8/1988 | Berry, Jr. |
| 4,923,471 A | 5/1990 | Morgan |
| 5,071,002 A | 12/1991 | Bradley |
| 5,762,211 A | 6/1998 | Ensign |
| 5,850,917 A | 12/1998 | Denton et al. |
| 6,142,314 A | 11/2000 | Cotterill |
| 6,802,421 B1 * | 10/2004 | Impellizzeri ........... A61B 50/20 206/438 |
| 6,827,913 B2 | 12/2004 | Wood |
| 7,603,788 B2 | 10/2009 | Kurz et al. |
| 8,061,517 B2 | 11/2011 | Loeffler et al. |
| 9,005,206 B2 | 4/2015 | Ampuero et al. |
| 9,179,977 B2 * | 11/2015 | Rigsby .................. A61B 17/70 |
| 9,498,294 B2 | 11/2016 | Rigsby et al. |
| 11,160,628 B2 * | 11/2021 | Ritchey ..................... A61J 1/00 |
| 2002/0052607 A1 | 5/2002 | Kennefick et al. |
| 2007/0095689 A1 | 5/2007 | Pratt et al. |
| 2007/0104609 A1 | 5/2007 | Powell |
| 2008/0230423 A1 | 9/2008 | Loeffler et al. |
| 2009/0266889 A1 | 10/2009 | Turner et al. |
| 2011/0297571 A1 | 12/2011 | Brand |
| 2012/0138495 A1 * | 6/2012 | Bettenhausen ........ A61B 50/30 206/339 |
| 2013/0001180 A1 | 1/2013 | Stout et al. |
| 2013/0119001 A1 | 5/2013 | Heede et al. |
| 2014/0202903 A1 | 7/2014 | Dassonville et al. |
| 2015/0122682 A1 | 5/2015 | Kerboul et al. |
| 2018/0064506 A1 | 3/2018 | Kieser et al. |

FOREIGN PATENT DOCUMENTS

| | | |
|---|---|---|
| GB | 2418421 A | 3/2006 |
| JP | 2007330449 B2 | 12/2007 |
| WO | 0149198 A1 | 7/2001 |
| WO | 2009024189 A2 | 2/2009 |

OTHER PUBLICATIONS

International Search Report and Written Opinion for International application No. PCT/US2014/063417, dated May 8, 2015, 18 pages.

\* cited by examiner

MEDICAL IMPLANT DELIVERY SYSTEM AND METHOD AND AN IMPLANT HAVING A DETACHABLE MARKING SECTION

CROSS REFERENCE TO RELATED APPLICATIONS

This application is a continuation application of U.S. patent application Ser. No. 16/421,739, filed May 24, 2019, which is a divisional application of U.S. patent application Ser. No. 15/033,482, filed Apr. 29, 2016, now abandoned, which is a U.S. National Phase filing of International Application No. PCT/US2014/063417, filed on Oct. 31, 2014, which claims the benefit of U.S. Provisional Application No. 61/898,531 filed Nov. 1, 2013, and also claims the benefit of U.S. Provisional Application No. 61/919,154 filed Dec. 20, 2013, the contents of each application incorporated herein by reference in their entirety.

BACKGROUND OF THE INVENTION

The present invention relates generally to providing medical implants for surgical use, and more particularly to providing one or more medical implants with associated holder mechanisms in a caddy where the medical implants and holder mechanisms are aligned in particular orientations in the caddy.

There is a continuing need to provide medical implants for surgical use in a way that is convenient and organized for surgical staff. In addition, there is a need to track medical implants from their base materials and manufacture through their use. Various regulatory bodies throughout the world have continued to impose stricter standards for such tracking. Tracking of non-sterile medical implants, i.e., medical implants that must be sterilized at the site of the surgery before each potential use, is challenging because traditionally such implants have been shipped in groups with other similar implants, but without specific tracking labeling. In recent years, many tracking packaging and labeling mechanisms have been developed which can be associated with each medical implant to be tracked and sold. However, many of these mechanisms have failed to provide medical implants and associated packaging that both allow for effective sterilization before each use and which also provide for convenient and organized presentation of the medical implants to surgical staff. For example, many of these prior devices provide medical implants and associated packaging that may be placed anywhere in a tray or caddy, and/or the medical implants are placed in any orientation relative to the tray or caddy regardless of the type or size of medical implant. Such mechanisms increase the risk that a medical implant will be placed incorrectly in a tray or caddy of medical implants and used inappropriately in surgery. To avoid such risks, medical staff must spend extra time sorting, arranging, and managing surgical trays or caddies used in association with such mechanisms. Alternatively, some individual tracking solutions label each medical implant separately, but fail to organize and present the medical implants to the surgical staff. This solution requires a larger amount of operating room space to effectively present the medical implants to surgical staff, and also increases the risk of mistaken selection of medical implants by the surgeon or surgical staff.

Improved mechanisms may provide a tray or caddy that is configured to receive medical implants and associated mechanisms that provide for both tracking and sterilization, and that present the medical implants in an organized fashion relative to the tray or caddy. One or both of orientation and location of medical implants in a tray or caddy may be controlled/arranged by size, shape, or other features via various improved mechanisms.

SUMMARY

An embodiment of the invention is directed to a caddy configured to receive a medical implant coupled to a holder. The caddy may include a substantially planar top element with a top surface and a bottom surface and having an opening that extends through the substantially planar top element, and a support structure coupled to the substantially planar top element on the bottom surface side such that the support structure provides a volume adjacent to the bottom surface configured to allow circulation of sterilization substances within the volume. In some embodiments, the opening through the substantially planar top element has a non-symmetrical shape about at least one primary axis of the substantially planar top element, with the opening configured to receive a matching non-symmetrically shaped holder to which a medical implant is coupled, such that when the holder and medical implant are received in the opening through the substantially planar top element, the holder is aligned in a predetermined orientation relative to the substantially planar top element.

Another embodiment of the invention is directed to a medical implant delivery system which may include a medical implant, a holder coupled to the medical implant that has a first area and a second area, wherein the second area is at least in part substantially perpendicular to the first area, one or more markings on the first area that include basic identifying information, and a caddy. The caddy may be configured to receive the holder coupled to the medical implant and include a substantially planar top element with a top surface and a bottom surface and having an opening that extends through the substantially planar top element, and a support structure coupled to the substantially planar top element on the bottom surface side such that the support structure provides a volume adjacent to the bottom surface configured to allow circulation of sterilization substances within the volume. In some embodiments, the opening through the substantially planar top element has a non-symmetrical shape about at least one primary axis of the substantially planar top element, wherein the opening is configured to receive a matching non-symmetrically shaped holder to which a medical implant is coupled, such that when the holder and medical implant are received in the opening through the substantially planar top element, the holder is aligned in a predetermined orientation relative to the substantially planar top element.

Yet another embodiment of the invention is directed to a method of providing a medical implant assembly that may include manufacturing a medical implant, providing a holder for the medical implant that has a first area and a second area, wherein the second area is at least in part substantially perpendicular to the first area, coupling the holder to the medical implant, and providing a caddy configured to receive the holder coupled to the medical implant and display the first area markings. Embodiments of the caddy include a substantially planar top element with a top surface and a bottom surface and having an opening that extends through the substantially planar top element, and a support structure coupled to the substantially planar top element on the bottom surface side such that the support structure provides a volume adjacent to the bottom surface configured to allow circulation of sterilization substances within the volume. In some embodiments, the opening through the substantially planar top element has a non-symmetrical shape about at least one primary axis of the substantially planar top element, wherein the opening is configured to receive a matching non-symmetrically shaped holder to which a medical implant is coupled, such that when the holder and medical implant are received in the opening through the substantially planar top element, the holder is aligned in a predetermined orientation relative to the substantially planar top element. The method may also include shipping the medical implant assembly.

Still another embodiment of the invention is directed to a method of providing a medical implant assembly that may include manufacturing a medical implant and packaging the medical implant with a holder. The medical implant and the holder may be contained within a package, and the holder may be marked with identifying information. This embodiment may also include sterilizing the medical implant and the holder while packaged, opening the package in which the medical implant and holder are packaged, placing the medical implant and the holder into a caddy, and re-sterilizing the medical implant and the holder while in the caddy.

A further embodiment of the invention is directed to a medical implant having an implant body portion and a detachable marking portion that is connected to the implant body portion by a frangible region structured to provide selective separation of the implant body portion from the detachable marking portion upon application of a specified force or torque to the implant body portion, and the detachable marking portion including one or more markings that correspond to identifying information associated with features or characteristics of the implant body portion.

BRIEF DESCRIPTION OF THE DRAWINGS

The accompanying drawings are incorporated in and form a part of the specification, illustrate the embodiments of the invention, and together with the written description serve to explain the principles, characteristics, and features of the invention. In the drawings.

DETAILED DESCRIPTION OF THE EMBODIMENTS

The following descriptions of the depicted embodiments are merely exemplary in nature and are in no way intended to limit the invention or its application and uses.

Figure 1:
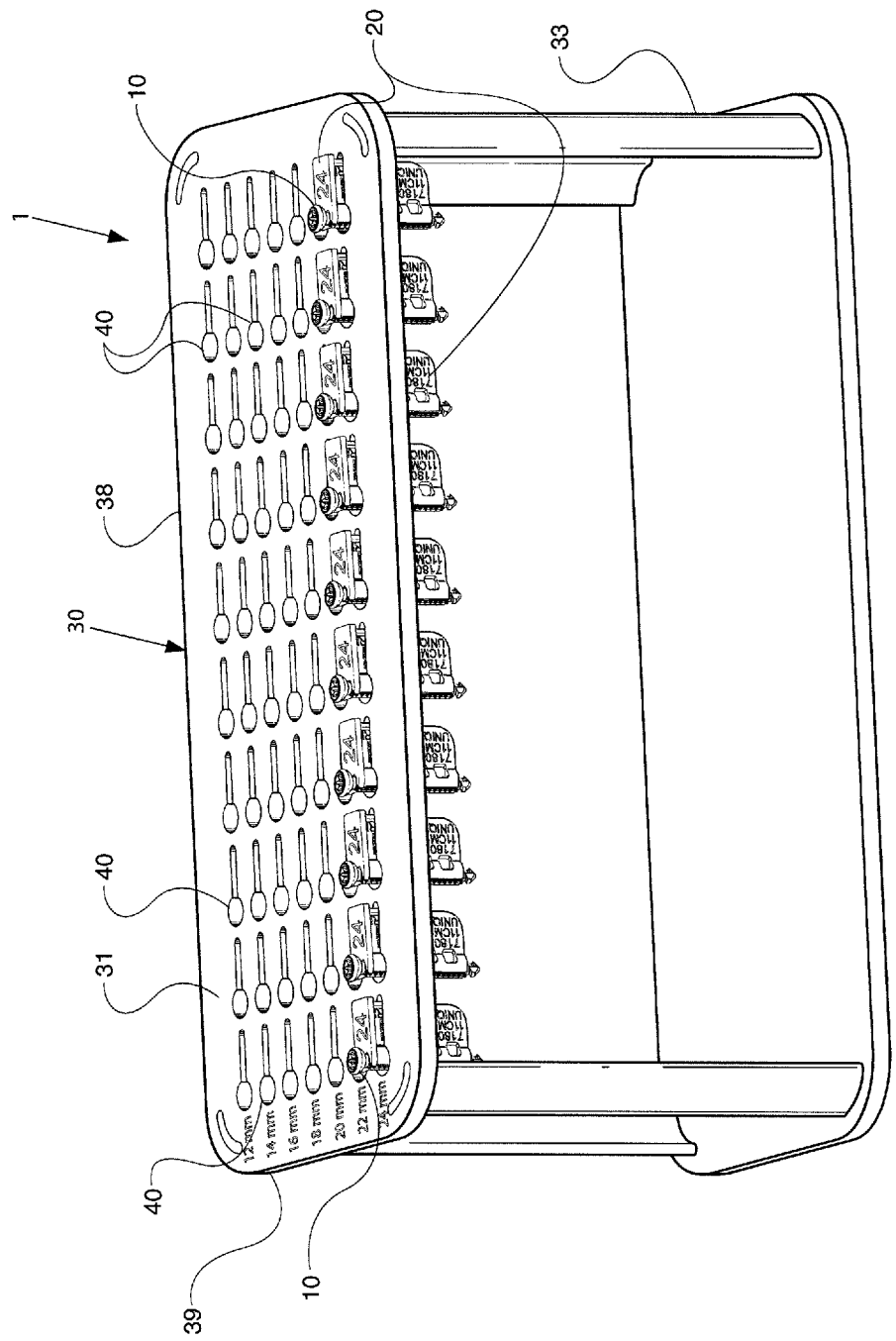
FIG. 1 is a perspective view of a system embodiment including a caddy embodiment with associated medical implants and holders.
Figure 2:
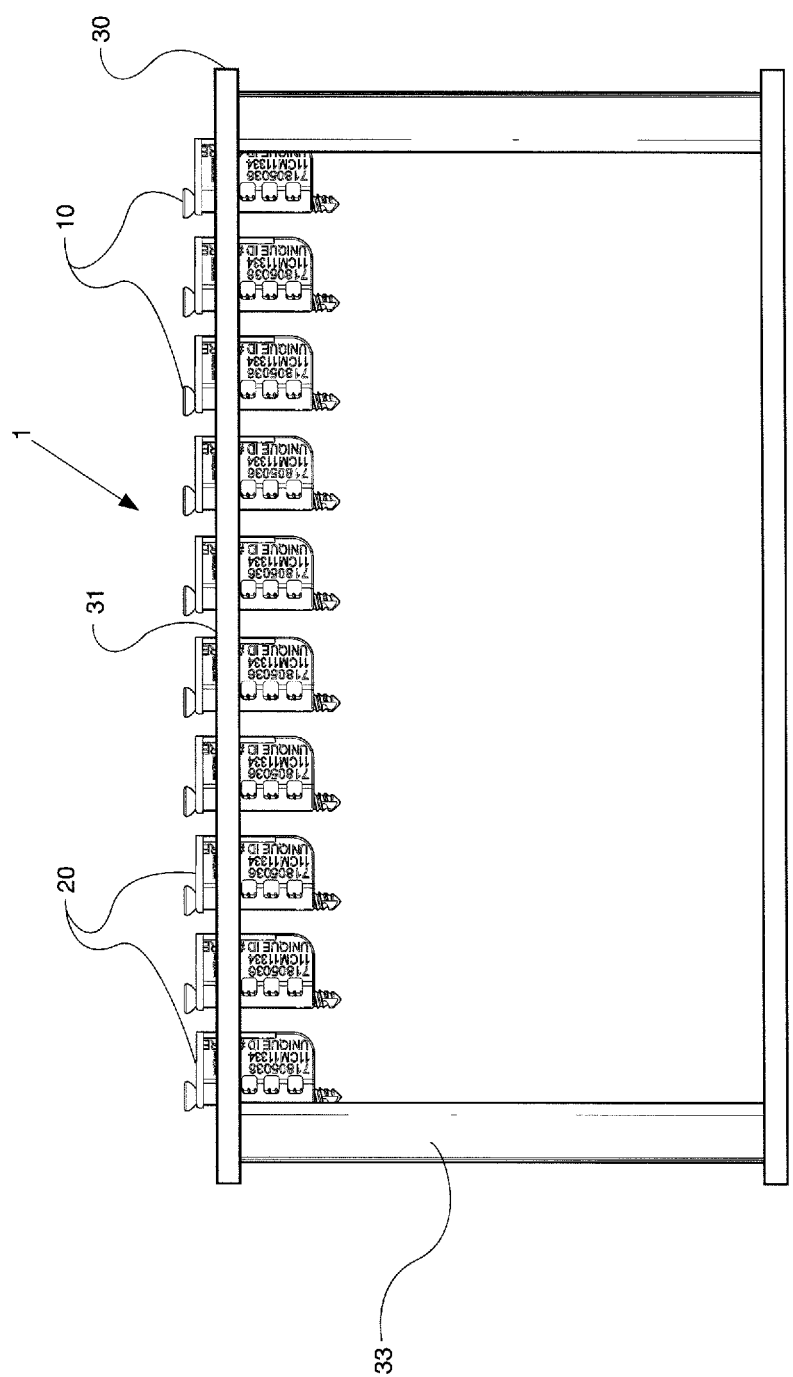
FIG. 2 is an elevation view of the system of FIG. 1.

One embodiment of a medical implant delivery system 1 is illustrated in FIGS. 1 and 2. In the illustrated embodiment, one or more medical implants 10 are coupled with respective holders 20. The implants 10 and holders 20 are shown as being supported in a caddy 30. In the illustrated embodiment, the medical implants 10 are configured as bone screws. However, in other embodiments, the medical implants may be configured as any type of medical implant or instrument that is recommended for sterilization prior to surgical use. Medical implants of some embodiments may not need to be sterilized, but may be more effectively organized or presented in the medical implant delivery system described herein. Non-limiting examples of medical implants of some embodiments may include other types of screws or fasteners and may be treated or untreated with other substances. Possible treatments include combination or coating with materials such as hydroxyapatite or polymers. Medical implants of some embodiments could be configured as washers, plates, rods, nuts, special types of screws, linkages, staples, tethers, wires, intramedullary nails, external fixation devices, hip prostheses, knee prostheses, any instrument useful with any of the previously recited devices, or any other type of device that may be used in a medical or surgical procedure.

Figure 3:
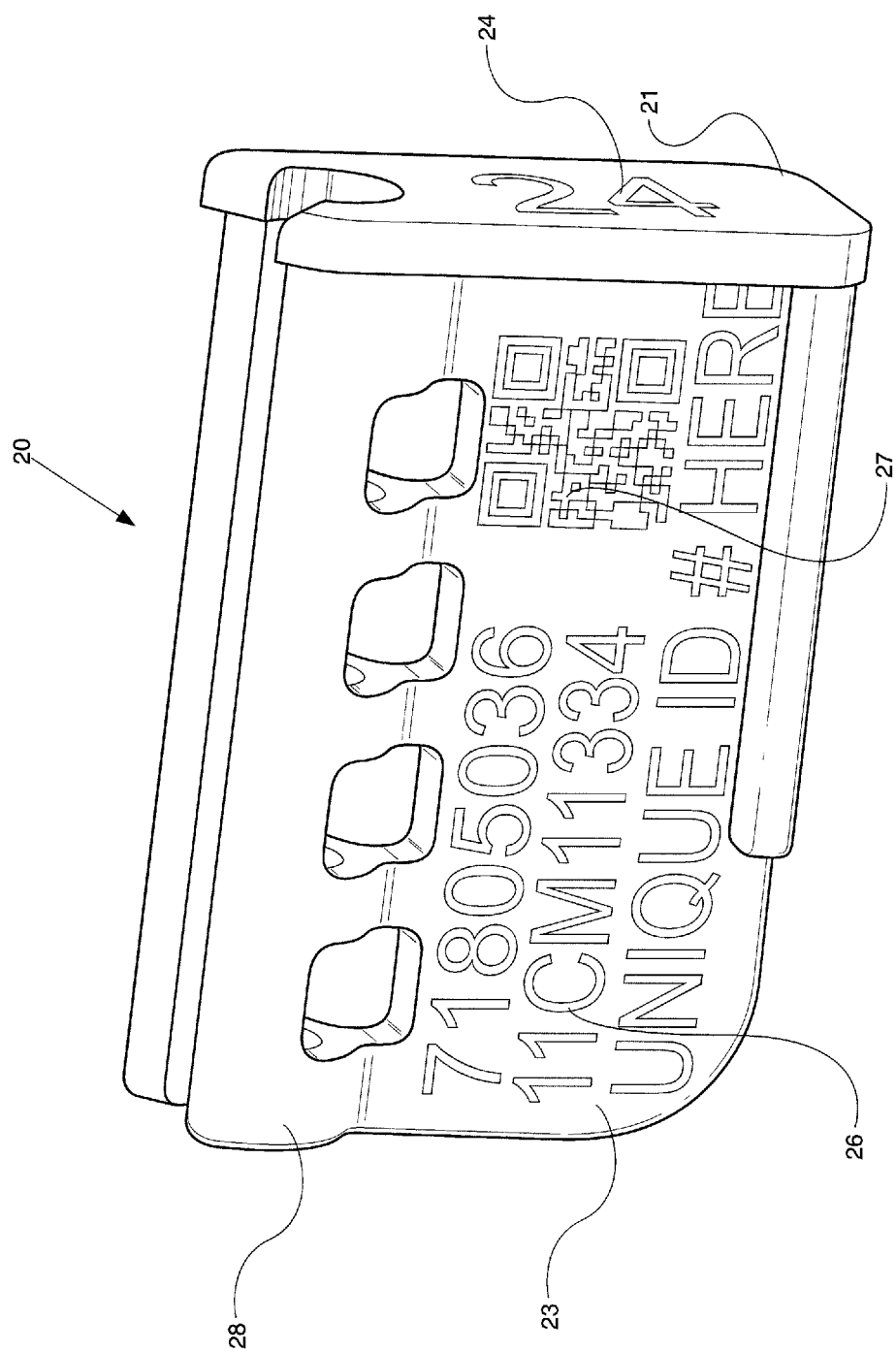
FIG. 3 is a perspective view of a holder for a medical implant.
Figure 4:
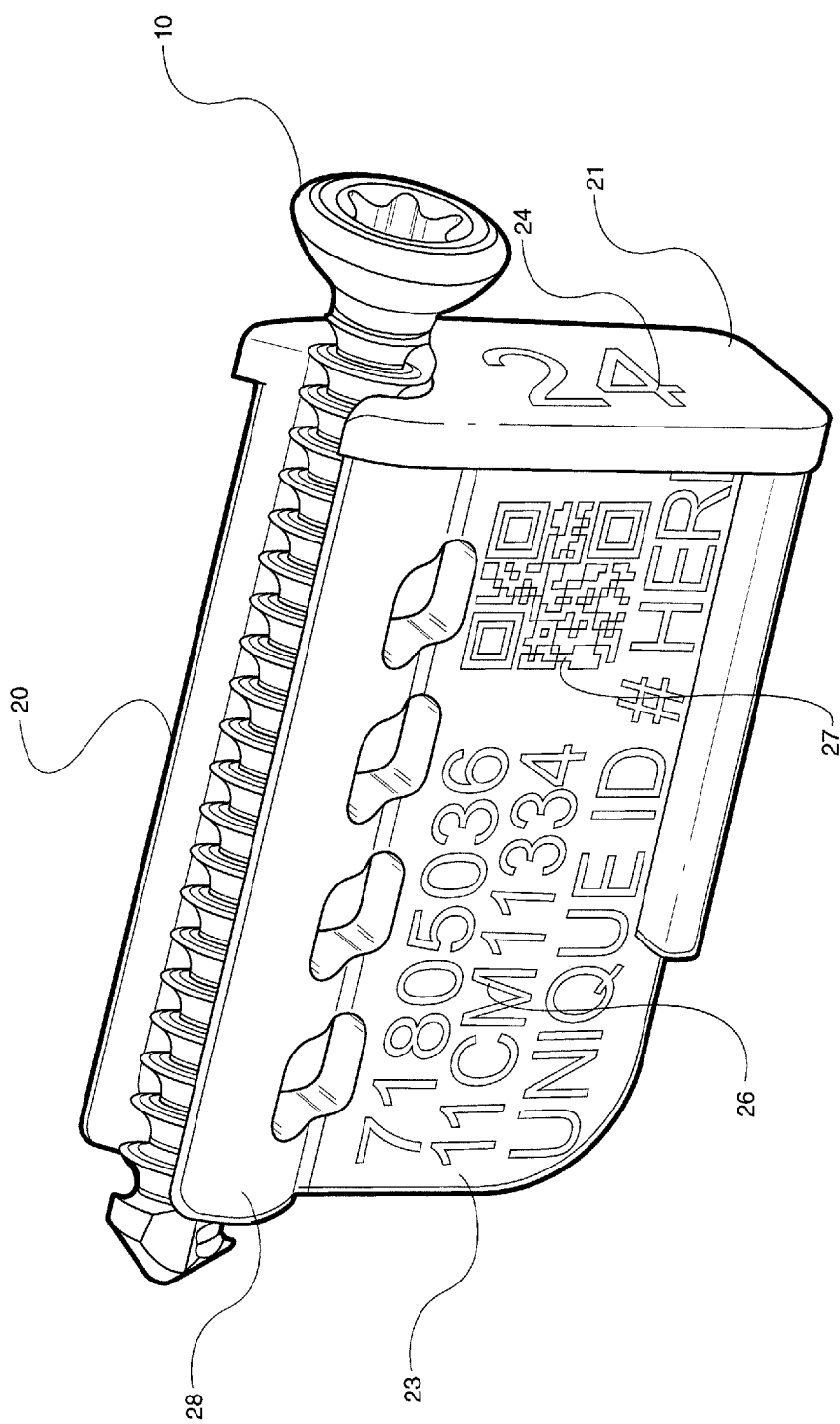
FIG. 4 is a perspective view of the holder of FIG. 3 coupled with a medical implant.

An embodiment of the holder 20 is illustrated in more detail in FIGS. 3 and 4. In the depicted embodiment, the holder 20 includes a top surface 21 and a side surface 23 that is at least in part substantially perpendicular to the top surface 21. In FIGS. 3 and 4, a marking or indicia 24 is shown on the top surface 21 that provides basic identifying information that corresponds to the medical implant 10. For example the number "24" of the marking 24 designates the medical implant 10 as a screw having a 24 mm length. Markings or indicia on the top surface of various embodiments of the holder 20 may relate to a length or another size parameter of any kind (i.e., height, width, diameter, etc.), or may present or abbreviate other information about an associated medical implant.

In the illustrated embodiment, the side surface 23 includes identifying information of greater detail by presentation of a detail marking or indicia 26. Information in the detail marking 26 may include, without limitation, one or more of material lot numbers, implant sizes, types, configurations, manufacturing lot numbers, dates, locations, a unique identification, or any other type of information or data relating to the medical implant 10 that is to be associated with a holder 20. Detail markings or indicia 26 may also include encoded data of any usable type including, without limitation, visual, electronic, or magnetic data, such as but not limited to barcodes, QR codes, microchips, and magnetic strips. One example of a detail marking 26 of encoded data is illustrated in FIGS. 3 and 4 as the QR code of the coded marking 27. Coded markings may duplicate data included in the detailed markings 26, or may include any or all of additional data, electronic links, and other references. The illustrated detail markings 26 have a greater surface area than the marking 24, as well as a greater number of characters or features. In the illustrated embodiment, the ratio of the area of the side surface 23 to the area of the top surface 21 is greater than three to one. However, various embodiments of the invention may include marking to detail markings area and character ratios of other proportions.

Markings or indicia on the top surface and the side surface may be applied or created by any effective or suitable mechanism or technique. For example and without limitation, the markings may be milled, molded, etched, printed, cut, or burned into various embodiments of the holder.

The holder 20 illustrated in FIGS. 1-5 has a non-symmetrically shaped cross-section perpendicular to its longitudinal axis. The cross-section of the holder 20 is non-symmetrical about one primary axis in the plane of the cross-section. However, some embodiments may include holders that are non-symmetrical about two primary axes in the plane of the cross-section. The cross-sectional shape of the illustrated holder 20 is substantially similar to the cross-sectional shape of a skeleton key, with a planar portion parallel with the side surface 23 and a cylindrical portion 28 (FIGS. 3 and 4) coupled along the planar portion.

Figure 5:
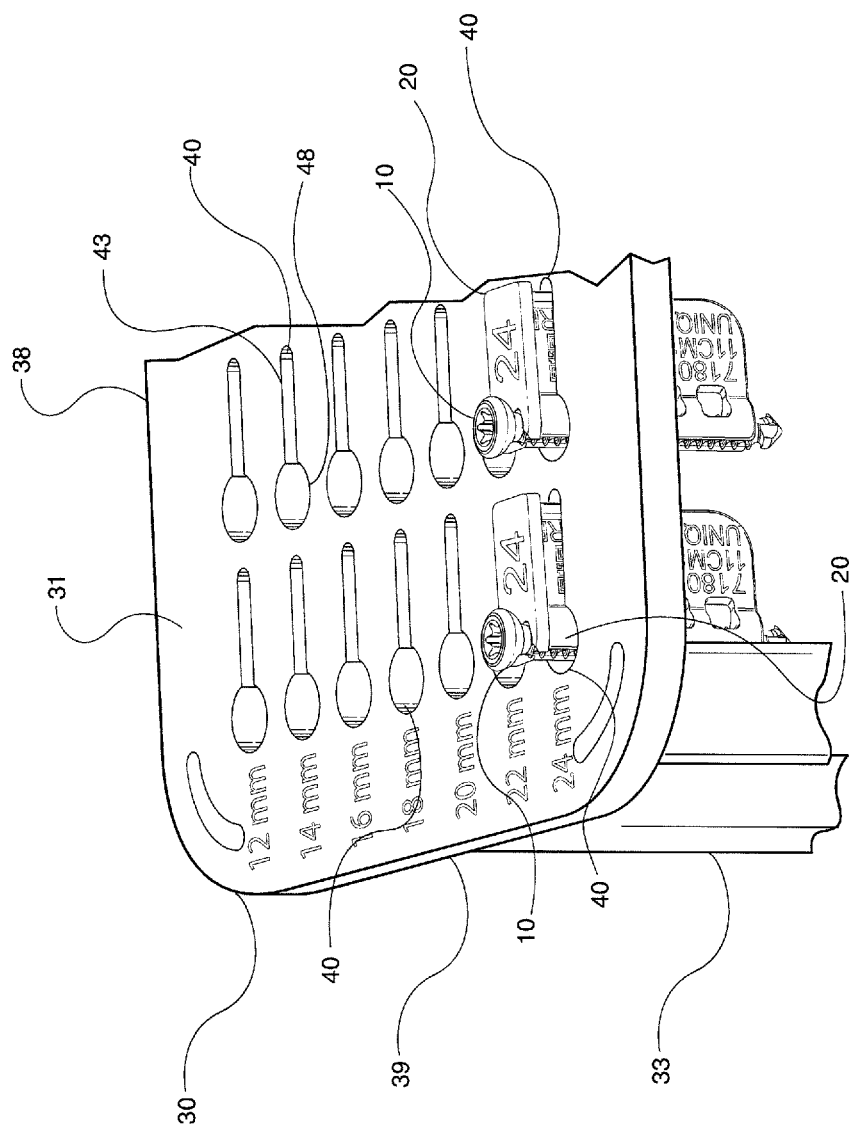
FIG. 5 is an enlarged perspective view of the system of FIG. 1.

The caddy 30 shown in FIGS. 1, 2 and 5 has a substantially planar top element 31 with a top surface and a bottom surface and a number of openings 40 that extend through the substantially planar top element 31. A support structure 33 is coupled to the substantially planar top element 31, as shown in FIGS. 1, 2 and 5. In the embodiment illustrated, the support structure 33 is coupled to the substantially planar top element 31 on the bottom surface of the substantially planar top element 31 to provide a volume adjacent to the bottom surface to allow circulation of sterilization substances within the volume. Sterilization substances may include steam or any other effective sterilization substance such as but not limited to ethylene oxide. Combinations of sterilization substances may also be used.

The openings 40 in the substantially planar top element 31 illustrated in FIGS. 1 and 5 have a non-symmetrical shape about at least one primary axis of the substantially planar top element 31. The primary axes of the substantially planar top element 31 in the illustrated embodiment are axes that are parallel to the sides 38, 39 of the substantially planar top element 31. In an exemplary opening 40 shown in FIG. 5, the opening 40 is non-symmetrically shaped about a primary axis parallel to the side 39. The illustrated opening 40 is configured to receive a matching non-symmetrically shaped holder such as, for example, the holder 20 to which the medical implant 10 is coupled. The holder 20 and implant 10 are considered to match the opening 40 as the term "match" is used herein. A "match" as used herein means an exact or a substantially common shape or perimeter. Some embodiments may include one or more openings that are non-symmetrical about two primary axes in the plane of the openings. The shape of the illustrated opening 40 is substantially similar to the shape of a skeleton key keyhole, with a substantially rectangular opening component 43 and an intersecting, adjacent substantially round opening component 48 (FIG. 5). In the illustrated embodiment, the substantially rectangular opening component 43 has one side dimension that is less than the diameter of the substantially round opening component 48. The term "diameter" used herein with reference to the substantially round opening component 48 does not connote that the component must be round, but refers to a largest extent or mean extent of the component. The substantially round opening component 48 is configured to receive the cylindrical portion 28, and the substantially rectangular opening component 43 is configured to receive the planar portion, which in the illustrated embodiment is parallel with the side surface 23. Other embodiments may include openings with other effective non-symmetrical shapes.

As illustrated in FIGS. 1, 2 and 5, when the holders 20 and medical implants 10 are received in the openings 40 through the substantially planar top element 31 of the caddy 30, the holders 20 are aligned in a predetermined orientation relative to the substantially planar top element 31. In particular, in this embodiment, the markings 24 of the multiple holders 20 are presented in readable orientations common with one another, and which are readable from the same orientation as the size labeling on the substantially planar top element 31 when the holders 20 and the medical implants 10 are received in the openings 40. Although, for clarity, multiple openings 40 in the illustrated embodiment are shown without received holders 20 and medical implants 10, in some embodiments, each of the openings 40 may be utilized.

Alternate embodiments of a caddy 130, 230, 330, 430 are illustrated in FIGS. 6-9, respectively. Each caddy 130, 230, 330, 430 includes four rows of openings rather than seven rows of openings, as is the case with the caddy 30. However, any effective number of rows or arrangement of openings are contemplated for various embodiments of the caddy.

Figure 6:
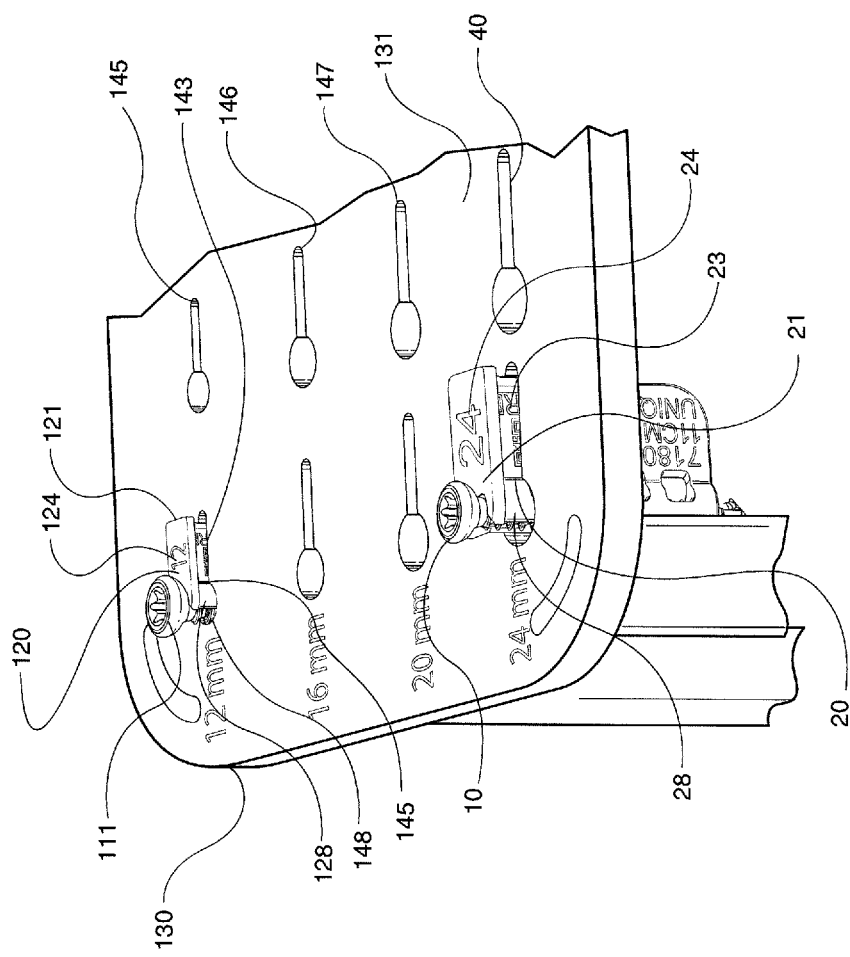
FIG. 6 is an enlarged perspective view of a system embodiment including a caddy embodiment with associated medical implants and holders.

Referring to FIG. 6, the caddy 130 includes a substantially planar top element 131 with openings 40, 145, 146, 147 that are similar in shape, but are provided with different sizes. Opening 145, for example, is substantially the shape of a skeleton key keyhole, with a substantially rectangular opening component 143 and an intersecting, adjacent substantially round opening component 148. The substantially round opening components of the openings 146, 147 and 40 are progressively smaller, in that order. The overall length of the openings 145, 146, 147 and 40 are progressively longer, in that order. Consequently, only one particular size of an available holder combined with medical implant may be received within each of the openings in the caddy 130. For example, a holder 120 includes a cylindrical portion 128 that has a larger diameter than any of the substantially round opening components of the openings 146, 147, 40, and therefore the holder 120 would not fit inside any of the openings 146, 147, 40. Similarly, the combined width of the planar portion parallel with the side surface 23 and the cylindrical portion 28 is longer than any of the openings 145, 146, and 147, and therefore the holder 20 would not fit inside any of the openings 145, 146, 147. By application of these mechanisms, when the holders and medical implants are received in the opening in which they will fit, the holders are positioned at predetermined locations in the caddy 130.

The caddy 130 includes size labeling or indicia for rows of 12 mm, 16 mm, 20 mm, and 24 mm long medical implants on the substantially planar top element 131. Correlating markings or indicia 24 are shown on the top surface 21 of the holder 20 which is configured to couple with a corresponding medical implant 10. Similarly, a correlating marking or indicia 124 (i.e., the number "12") is shown on the top surface 121 of the holder 120. The designator "12" in this example designates a medical implant that is 12 mm long, which in this embodiment corresponds to the medical implant 111. As describe herein, openings 40, 145, 146, and 147 are of different sizes. In this embodiment, the different sizes of the openings correlate with medical implants of different sizes.

Figure 7:
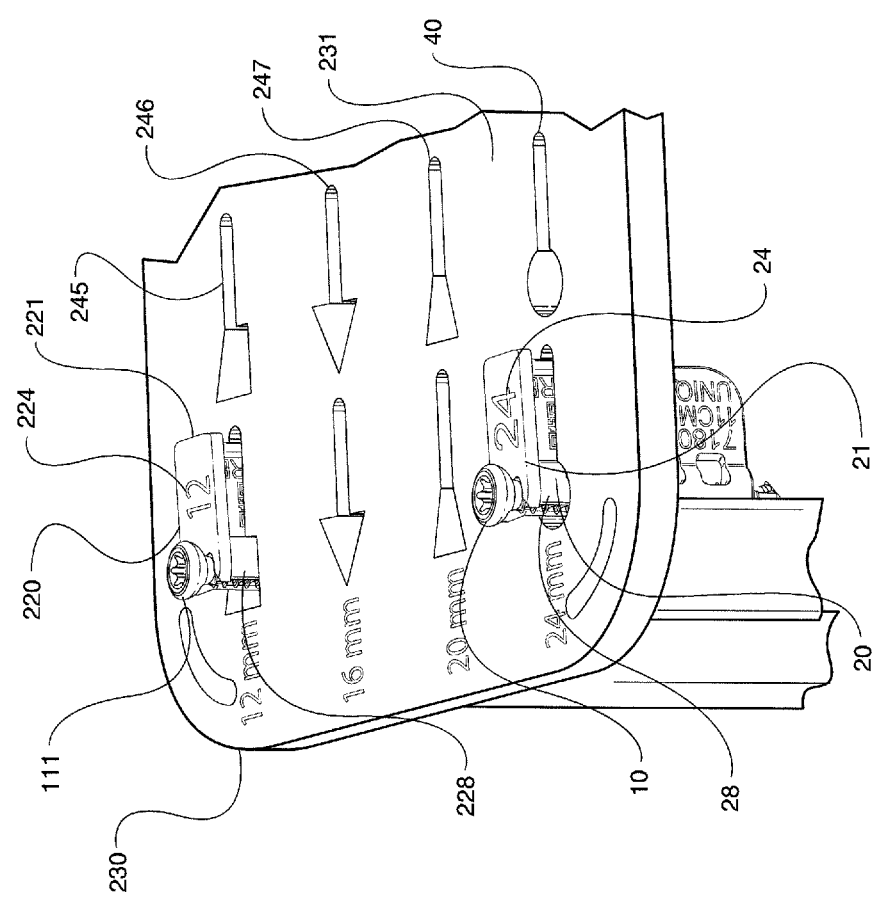
FIG. 7 is an enlarged perspective view of a system embodiment including a caddy embodiment with associated medical implants and holders.

Referring to FIG. 7, the caddy 230 includes a substantially planar top element 231 with openings 40, 245, 246, 247 that are similar in size, but have different shapes. Opening 40, for example, is substantially the shape of a skeleton key keyhole, as described above. Opening 247 includes a substantially rectangular opening component and an intersecting, adjacent substantially triangular opening component. Opening 246 includes a substantially rectangular opening component and an intersecting, adjacent substantially triangular opening component oriented opposite from the triangular opening component of the opening 247. Opening 245 includes a substantially rectangular opening component and an intersecting, adjacent irregular polygonal opening component. Consequently, only one shape of an available holder combined with a corresponding medical implant may be received within each of the openings in the caddy 230. For example, a holder 220 that includes an irregular polygonal portion 228 will not fit in any of the openings 246, 247 and 40. Similarly the cylindrical portion 28 of the holder 20 would interfere with one or more of each of the converging sides of the openings 245, 246 and 247, and thereby prevent the holder 20 from being received within any of the openings 245, 246 and 247. By application of these mechanisms, when the holders and medical implants are received in the opening in which they will fit, the holders are positioned at predetermined locations in the caddy 230.

The caddy 230 includes size labeling or indicia for rows of 12 mm, 16 mm, 20 mm, and 24 mm long medical implants on the substantially planar top element 231. Correlating marking or indicia 24 are shown on the top surface 21 of the holder 20 which is configured to couple with the medical implant 10. Similarly, correlating marking or indicia 224 (i.e., the number "12") is shown on the top surface 221 of the holder 220. The designator "12" in this example is used to designate a medical implant that is 12 mm long, which in this embodiment corresponds to the medical implant 111. As describe herein, openings 40, 145, 146 and 147 have different shapes. In this embodiment, the different shapes of the openings correlate with medical implants having different sizes.

Figure 8:
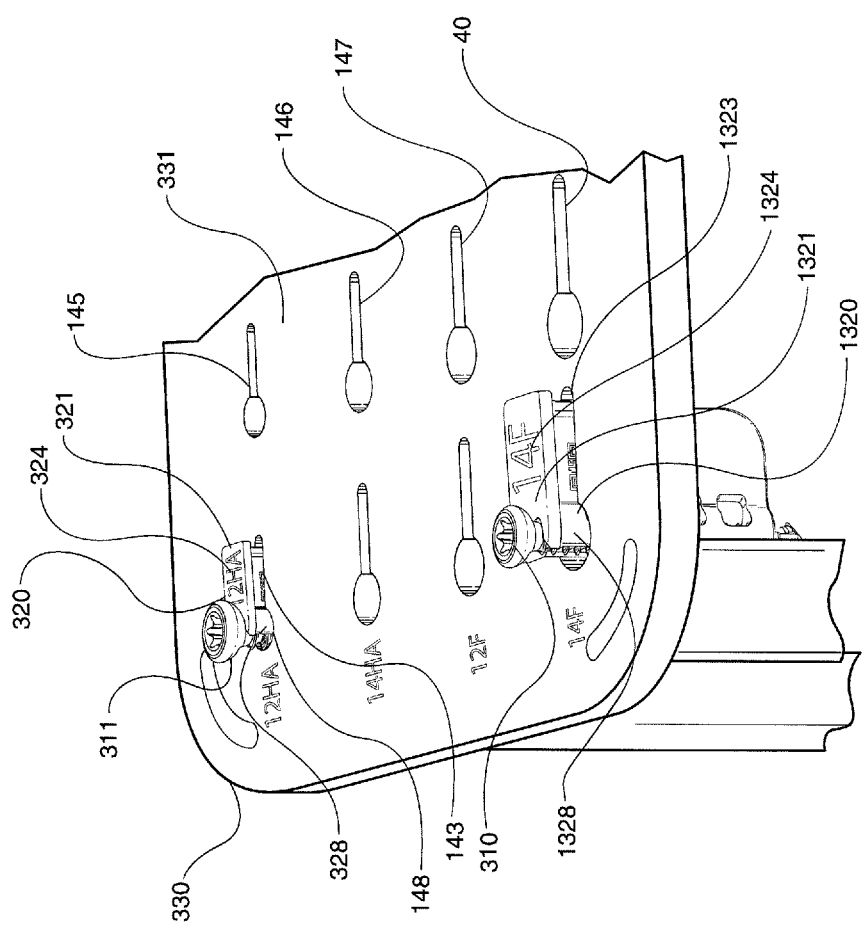
FIG. 8 is an enlarged perspective view of a system embodiment including a caddy embodiment with associated medical implants and holders.

Referring to FIG. 8, the caddy 330 includes a substantially planar top element 331 with openings 40, 145, 146, 147 that are similar in shape, but are provided with different sizes. Opening 145, for example, is substantially the shape of a skeleton key keyhole with a substantially rectangular opening component 143 and an intersecting, adjacent substantially round opening component 148. The substantially round opening components of openings 146, 147 and 40 are progressively smaller, in that order. The overall length of the openings 145, 146, 147 and 40 are progressively longer, in that order. Consequently, only one size of an available holder combined with a corresponding medical implant may be received within each of the openings in the caddy 330. For example, a holder 320 includes a cylindrical portion 328 that has a larger diameter than any of the substantially round opening components of the openings 146, 147, 40, and therefore the holder 320 would not fit inside any of the openings 146, 147, 40. Similarly, the combined width of the planar portion parallel with a side surface 1323 and a cylindrical portion 1328 is longer than any of the openings 145, 146 and 147, and therefore the holder 1320 would not fit inside any of the openings 145, 146, 147. By application of these mechanisms, when the holders and medical implants are received in the opening in which they will fit, the holders are positioned at predetermined locations in the caddy 330.

The caddy 330 includes size and type labeling or indicia for rows of 12 HA, 14 HA, 12F and 14F medical implants on the substantially planar top element 331. In this example, the number corresponds to a length designation, and the HA and F indicate hydroxyapatite coating and fenestrated, respectively. Therefore, for example, 12HA is labeling for a 12 mm long hydroxyapatite coated medical implant. Correlating marking or indicia 324, "12HA", is shown on the top surface 321 of the holder 320, which is configured to couple with the medical implant 311. Similarly, correlating marking or indicia 1324, "14F", is shown on the top surface 1321 of the holder 1320, which is configured to couple with the medical implant 310. As describe herein, openings 40, 145, 146 and 147 have different sizes. In this embodiment, the different sizes of the openings correlate with medical implants having different types and different sizes.

Figure 9:
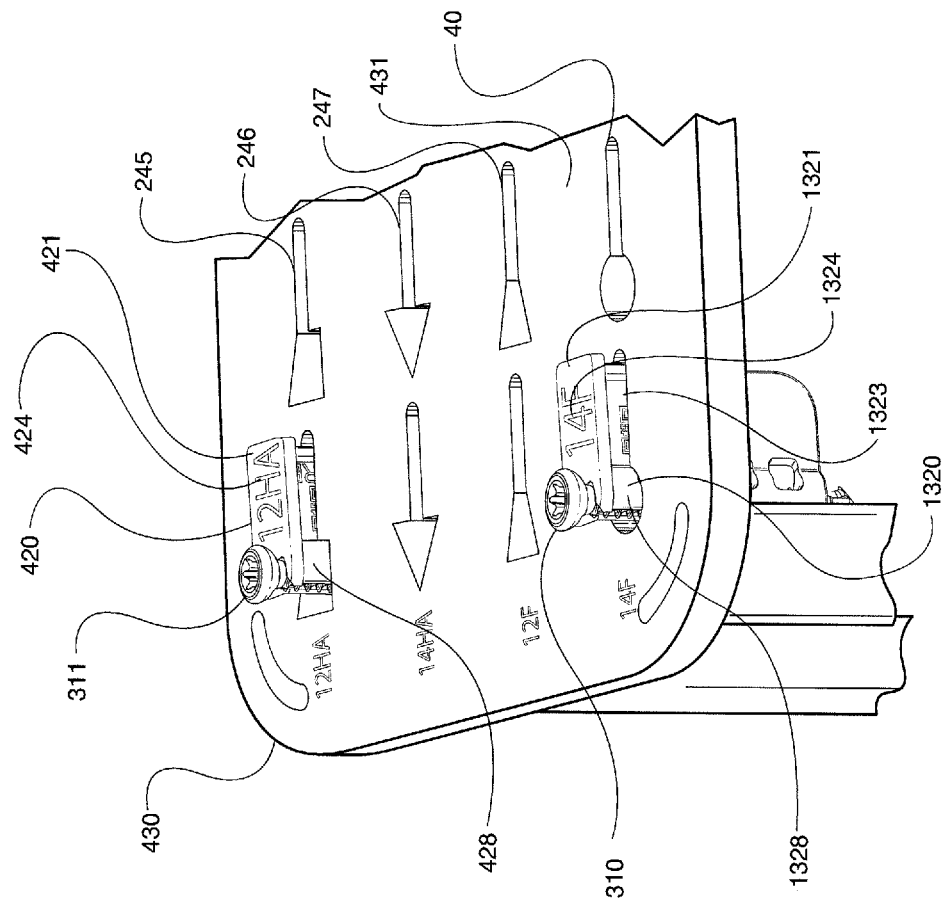
FIG. 9 is an enlarged perspective view of a system embodiment including a caddy embodiment with associated medical implants and holders.

Referring to FIG. 9, the caddy 430 includes a substantially planar top element 431 with openings 40, 245, 246, 247 that are similar in size, but which have different shapes. Opening 40, for example, is substantially the shape of a skeleton key keyhole, as described above. Opening 247 includes a substantially rectangular opening component and an intersecting, adjacent substantially triangular opening component. Opening 246 includes a substantially rectangular opening component and an intersecting, adjacent substantially triangular opening component oriented opposite from the triangular opening component of the opening 247. Opening 245 includes a substantially rectangular opening component and an intersecting, adjacent irregular polygonal opening component. Consequently, only one shape of an available holder combined with a corresponding medical implant may be received within each of the openings in the caddy 430. For example, a holder 420 that includes an irregular polygonal portion 428 will not fit in any of the openings 246, 247 and 40. Similarly the cylindrical portion 1328 of the holder 1320 would interfere with one or more of each of the converging sides of the openings 245, 246 and 247 and thereby prevent the holder 1320 from being received within any of the openings 245, 246 and 247. By application of these mechanisms, when the holders and medical implants are received in the opening in which they will fit, the holders are positioned at predetermined locations in the caddy 430.

The caddy 430 includes size and type labeling or indicia for rows of 12 HA, 14 HA, 12F and 14F medical implants on the substantially planar top element 431. In this example, the number corresponds to a length designation, and the HA and F indicate a hydroxyapatite coating and fenestrated, respectively. Therefore, for example, 12HA is labeling or indicia for a 12 mm long hydroxyapatite coated medical implant. Correlating marking or indicia 424, "12HA", is shown on the top surface 421 of the holder 420, which is configured to couple with a corresponding medical implant 311. Similarly, correlating marking or indicia 1324, "14F", is shown on the top surface 1321 of the holder 1320, which is configured to couple with a corresponding medical implant 310. As describe herein, openings 40, 245, 246 and 247 have different sizes. In this embodiment, the different types of the openings correlate with medical implants having different types and different sizes.

Various embodiments of devices described herein wholly or their parts individually may be made from any biocompatible material. The medical implant of some embodiments is capable of undergoing one or more steam sterilization cycles, or other sterilization procedures, without degrading in a manner that would make the implant unsuitable for use in a medical or surgical procedure. For example and without limitation, biocompatible materials may include, in whole or in part: non-reinforced polymers, reinforced polymers, metals, ceramics and combinations of these materials. Reinforcing of polymers may be accomplished with carbon, metal, or glass or any other effective material. Examples of biocompatible polymer materials include polyamide base resins, polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, tantalum, titanium, titanium alloys, titanium-nickel alloys such as Nitinol and other superelastic or shape-memory metal alloys. Components described herein may be formed by conventional milling or casting processes, by any type of three-dimensional printing or deposition based processes, or by any other effective or suitable process.

One embodiment of the invention is directed to a method of providing a medical implant assembly that may include manufacturing a medical implant. For example, medical implants may include devices such as medical implants 10, 111, 310 and 311 described herein. Method embodiments may also include providing a holder for the medical implant that has a first area and a second area, wherein the second area is at least in part substantially perpendicular to the first area. Exemplary holders described herein include holders 20, 120, 220, 320, 420 and 1320, each having respective top surfaces and side surfaces that embody the first area and the second area. Method embodiments may also include coupling the holders to the medical implants, and providing a caddy configured to receive the holder coupled to the medical implant and display the first area markings or indicia.

One embodiment of the invention is directed to a method of providing a medical implant assembly that may include manufacturing a medical implant and packaging the medical implant with a holder. Manufactured medical implants may include devices such as medical implants 10, 111, 310 and 311 described herein. Exemplary holders are described herein and include holder 20, 120, 220, 320, 420 and 1320. The medical implants and holders of various embodiments may be packaged within any effective of suitable package or device that contains them. Exemplary packaging may include materials that are resistant to the passing of toxins, bacteria, viruses, and other unwanted substances, but which permit one or more of sterilization substances and sterilizing energy transmissions to pass through to the medical implant and the holder. For example and without limitation, such a sterilization substance may include ethylene oxide. A non-limiting example of a sterilizing energy transmission is gamma radiation. In some embodiments, the packaging used may provide a substantially hermetically sealed package.

Embodiments of the holder are marked with identifying information. Identifying information may include one or both of information about the implant or type of implant generally, and/or specific information about the manufacture and use of the implant. Exemplary types of identifying information that may be employed include a device identifier and a production identifier, as defined by the U.S. Food and Drug Administration as part of Unique Device Identification ("UDI") guidance and rules. A UDI is a unique numeric or alphanumeric code that consists of two parts:

1.) a device identifier, a mandatory, fixed portion of a UDI that identifies the labeler or manufacturer and the specific version or model of a device; and
2.) a production identifier, a conditional, variable portion of a UDI that identifies one or more of the following when included:
   the lot or batch number within which a device was manufactured,
   the serial number of a specific device,
   the expiration date of a specific device,
   the date a specific device was manufactured, and/or
   the distinct identification code required by § 1271.290 (c) for a human cell, tissue, or cellular and tissue-based product regulated as a device.

Another act of some method embodiments includes sterilizing the medical implant and the holder. Any effective sterilization method or substance may be used in various embodiments. Sterilization may be accomplished at one or more of the following stages: prior to packaging, while packaged, and after removal from a package.

In one exemplary embodiment, sterilization may be accomplished while the medical implant and holder are packaged, the package may be opened, and the medical implant and holder may be placed in a caddy. While in the caddy, the medical implant and holder may be re-sterilized one or more times. For example, a replacement medical implant and holder may be supplied to a caddy as part of an array of medical implants and holders. The medical implant and holder may remain in the caddy until the particular size or type of medical implant is required for a medical or surgical procedure. Until the size or type of the medical implant is used, the medical implant may be re-sterilized with the caddy before each procedure in which the caddy is present. For example and without limitation, re-sterilization may be accomplished with an autoclave device. In some embodiments, a medical implant and holder unpackaged in a sterile environment that had been sterilized prior to shipment could be used in a surgical procedure without re-sterilization.

Embodiments of the caddy 30, 130, 230, 330, 430 include a substantially planar top element 31, 131, 231, 331, 431 with a top surface and a bottom surface and having an opening 40, 145, 146, 147, 245, 246, 247 that extends through the substantially planar top element, and a support structure coupled to the substantially planar top element on the bottom surface side such that the support structure provides a volume adjacent to the bottom surface configured to allow circulation of sterilization substances within the volume. In some embodiments, the opening through the substantially planar top element has a non-symmetrical shape about at least one primary axis of the substantially planar top element, wherein the opening is configured to receive a matching non-symmetrically shaped holder to which a medical implant is coupled, such that when the holder and medical implant are received in the opening through the substantially planar top element, the holder is aligned in a predetermined orientation relative to the substantially planar top element. Features of the caddy 30, 130, 230, 330, 430 are described in detail herein. In some embodiments, providing a caddy may include providing a caddy wherein the substantially planar top element 31, 131, 231, 331, 431 includes two or more types of non-symmetrically shaped openings of different types configured to receive two or more respectively matching non-symmetrically shaped holders to which medical implants are coupled, wherein each type of non-symmetrically shaped holder to which a medical implant is coupled can only be received in one type of non-symmetrically shaped opening in the caddy. Exemplary openings of different types and respectively matching non-symmetrically shaped holders to which medical implants are coupled are illustrated in FIGS. 6-9.

Method embodiments may also include shipping the medical implant assembly. Shipping of various embodiments may include intra-company and external shipping of all or part of the components of the medical implant assembly. For example, components of the assembly may be manufactured or processed in different locations and shipped intra-company to a facility where company personnel or a third party assemble all or a part of the medical implant assembly for final use by a customer. Alternatively or additionally, all or part of the medical implant assembly may be shipped away from company facilities for further manufacturing or processing. In some embodiments, complete medical implant assembly may be shipped directly to customers.

Referring to FIGS. 10-16, other embodiments of the present invention may provide an implant having a detachable marking section. In the illustrated embodiments, the implant is configured as a fastener, although other orthopaedic implants could also be used. For example, the implant could be configured as a pin, a hole plug, a staple, a rod, an intramedullary nail, a lag screw, a compression screw, a locking screw, non-locking screw, cannulated screw, a washer, a plate, a nut, a linkage, a tether, a wire, external fixation devices, hip prostheses, knee prostheses, any instrument useful with any of the previously recited devices, or any other type of device or instrument that may be used in a medical or surgical procedure.

The implant may be made from metal, plastic, or a composite. Exemplary materials include titanium, stainless steel, cobalt chrome, carbon composite, polyetheretherketone (PEEK), polyethylene, ultra high molecular weight polyethylene (UHMWPE), resorbable polylactic acid (PLA), and polyglycolic acid (PGA). Although the list of materials includes many typical materials out of which implants are made, it should be understood that implants made from any appropriate or suitable material fall within the scope of the invention. The implant may be treated or untreated with other substances. Possible treatments include combination or coating with materials such as, for example, hydroxyapatite or polymers.

Figure 10:
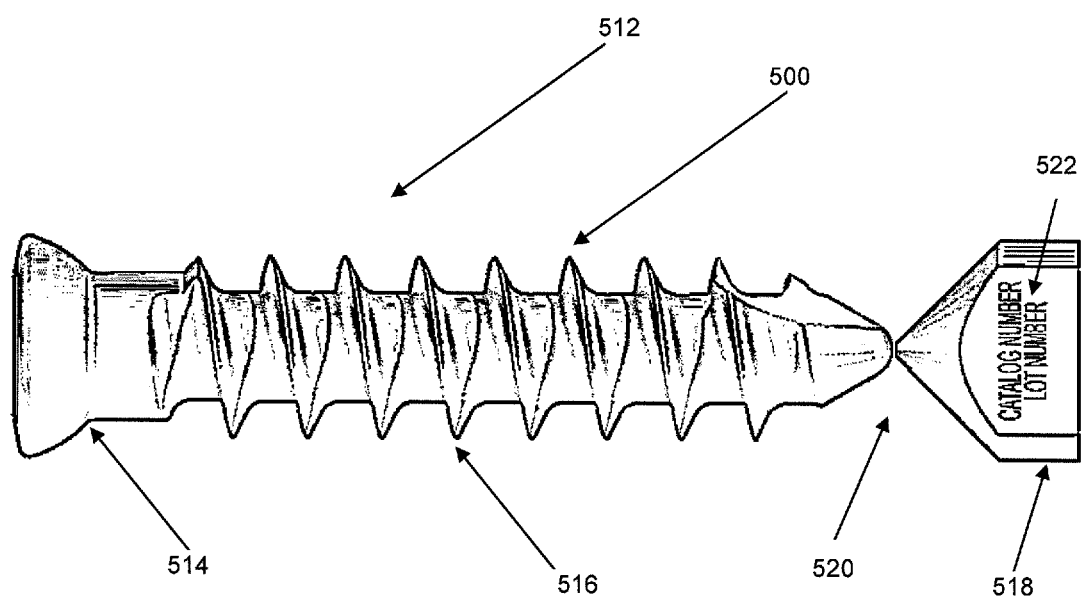
FIG. 10 is a side perspective view of a medical implant with a detachable marking section.

FIG. 10 shows a side perspective view of an implant 500 having a first portion 512 and a detachable marking or indicia section 518. In the depicted embodiment, the first portion 512 is configured as a fastener with a head portion 514 and a shaft portion 516. The detachable marking section 518 is connected to the first portion 512 via a frangible region 520 structured and configured to provide selective separation of the first portion 512 from the detachable marking section 518. The detachable marking section 518 may separate from the first portion 512 of the implant 500 at a specified force or torque. Additionally, the detachable marking section 518 may separate under shear, tension, bending or any combination of applied force or loading.

The detachable marking section 518 includes a marking or indicia 522 corresponding to the size or configuration of the first portion 512 of the implant 500. In some embodiments, the marking or indicia 522 provides basic identifying information. For example the number "24" of the marking 522 designates the implant 510 as a 24 mm long screw. Markings or indicia 522 of various embodiments may relate to features and/or characteristics of the implant portion including, for example, a length or other size parameters of any kind, or may present or abbreviate other information corresponding to an associated medical implant. While the depicted embodiment illustrates only one surface as having one marking or indicia 522, the detachable marking section 518 may include a plurality of surfaces, each having one or more markings or indicia 522. Information associated with the marking or indicia 522 may also include, without limitation, one or more of material lot numbers, implant sizes, types, configurations, manufacturing lot numbers, dates, locations, and a unique identification number for each medical implant 500. Markings or indicia 522 may also include encoded data of any usable or suitable type including, without limitation, visual, electronic, or magnetic data, such as but not limited to barcodes, QR codes, microchips, and magnetic strips. Coded markings may duplicate data included in the markings or indicia 522, or may include any or all of additional data, electronic links, and other references. Markings or indicia 522 may be applied or created by any effective mechanism or technique. For example and without limitation, the markings or indicia 522 may be milled, molded, etched, printed, cut, or burned into various embodiments.

Figures 11, 12:
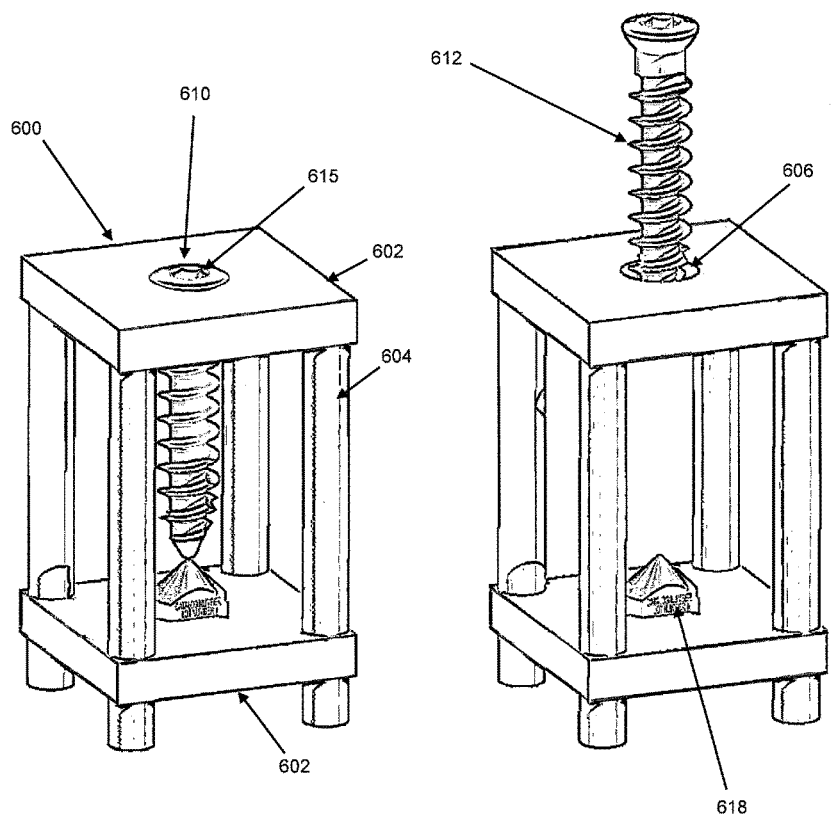
FIGS. 11 and 12 are side perspective views of an implant holder for use with a medical implant and a marking section.
Figure 13:
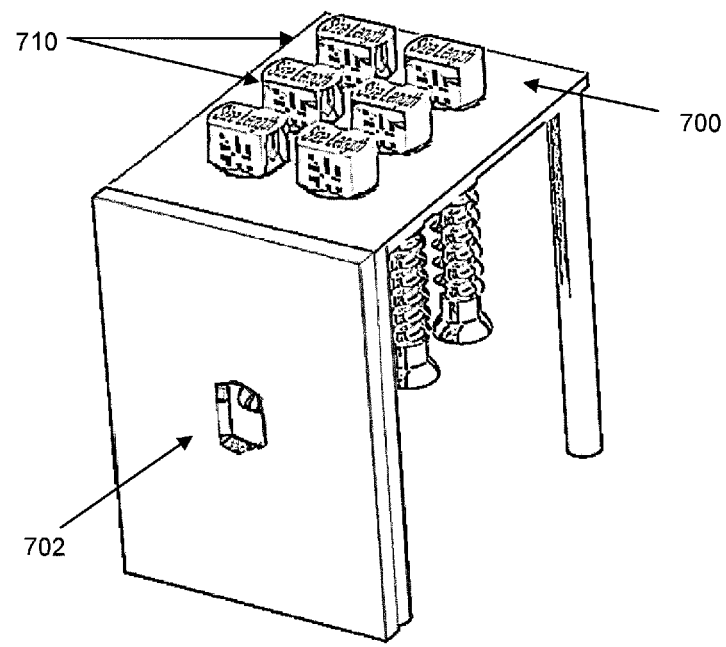
FIGS. 13-16 are side perspective views of a container for holding a number of medical implants.
Figure 14:
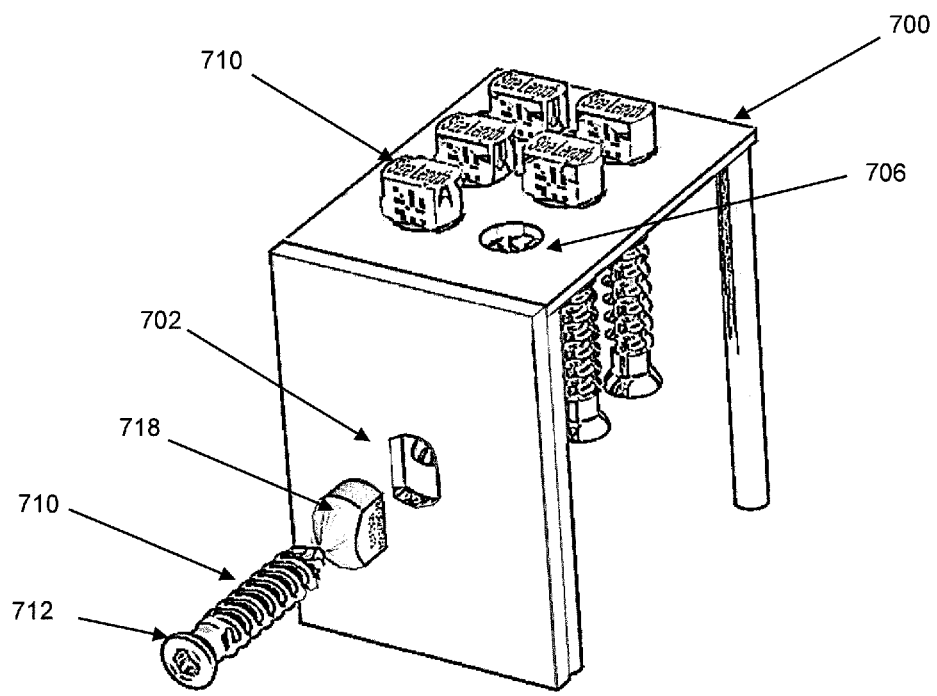
Figure 15:
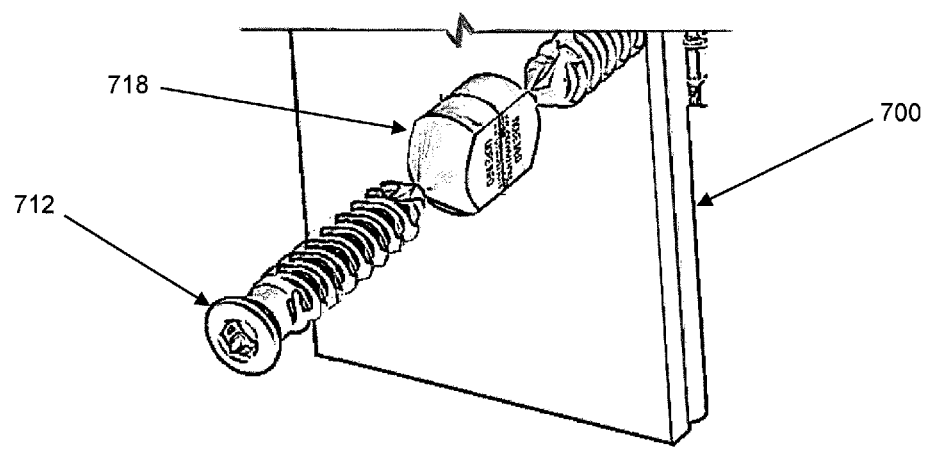
Figure 16:
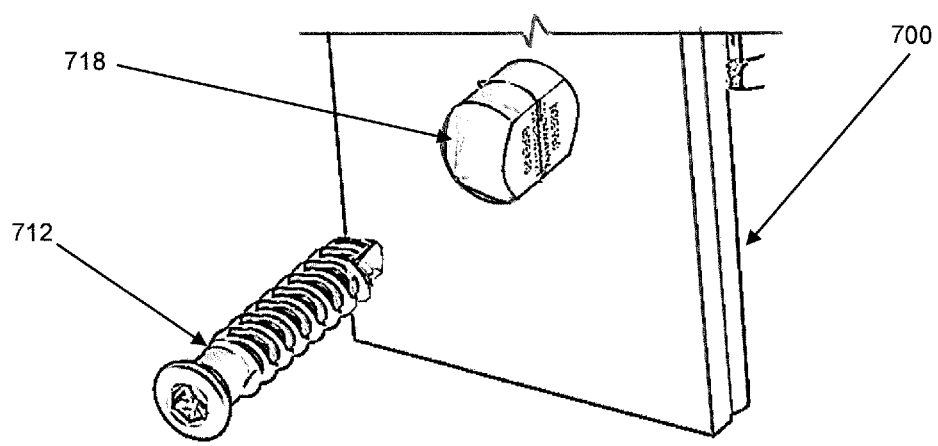

FIGS. 11-12 illustrate side perspective views of an implant holder 600 for holding an implant 610. The implant holder 600 may be manufactured in combination with the implant 610 such as, for example, by 3-D printing. A user removes a first portion 612 of the implant 610 such as, for example, by applying a torque to the implant 610. The first portion 612 separates from a detachable marking portion 618 of the implant 610, with the detachable marking portion 618 remaining attached to or coupled with the implant holder 600. In the depicted embodiment, the implant holder 600 includes two plates 602 separated and interconnected by four columns or supports 604. However, it should be understood that any number of plates 602 and/or columns 604 may be used. In some embodiments, the upper plate 602 has an opening 606 extending therethrough (FIG. 12). In the depicted embodiment, the columns 604 are round, but other shapes, such as rectangular or triangular, may also be used. The implant 610 may include a driven portion 615 (FIG. 11). In the depicted embodiment, the driven portion 615 is a hexagonal socket. However, other shapes and configurations of the driven portion 615 could also be used.

FIGS. 13-16 illustrate a container 700 for holding a plurality of implants 710. The container 700 includes a plurality of openings 706 that are each configured to receive an implant 710. In the depicted embodiment, the implants 710 are placed in the openings 706 and suspended by a detachable section 718 of the implant 710. The container 700 may also include a hole, passage or recess 702. The hole 702 may be used to remove the detachable marking section 718. In some embodiments, the hole 702 is sized and shaped to match the size and shape of the detachable marking section 718. In the depicted embodiment, the detachable marking section 718 has two planar side portions and two curvilinear end portions extending between the planar side portions. In one example, a user may place the detachable section 718 in the hole 702 and apply a torque to the first portion 712 to separate the first portion 712 from the detachable marking section 718. The material used for the container 700 may be somewhat reflective, with reflections of the implant including the first portion 712 and the detachable marking section 718 shown in FIGS. 15 and 16 via a side plate portion of the container 700. Although the container material could be reflective, it does necessarily need to be reflective.

Terms such as top, bottom, side, and the like have been used as relative terms herein. However, such terms are not limited to specific coordinate orientations, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the invention should not be limited by any of the above-described exemplary embodiments, but should be defined only in accordance with the claims and their equivalents.

What is claimed is:

1. A medical implant delivery system comprising:
a plurality of medical implants;
a plurality of non-symmetrically shaped holders, each one of the plurality of medical implants coupled to one of the plurality of non-symmetrically shaped holders; and
a caddy including:
a planar top element having a top surface, a bottom surface, and a plurality of openings extending through the planar top element from the top surface to the bottom surface; and
a support structure coupled to the planar top element on the bottom surface such that the support structure provides a volume adjacent to the bottom surface configured to allow circulation of sterilization substances within the volume; and
wherein the plurality of openings through the planar top element have a non-symmetrical shape about at least one primary axis of the planar top element, wherein each of the plurality of openings are configured to receive one of the plurality of non-symmetrically shaped holders to which one of the plurality of medical implants is coupled, such that when the holder and the medical implant are received in the opening through the planar top element, the holder is aligned in a predetermined orientation relative to the planar top element.

2. The medical implant delivery system of claim 1, wherein the plurality of openings through the planar top element are non-symmetrical about only one primary axis in the plane of the planar top element.

3. The medical implant delivery system of claim 1, wherein the plurality of openings through the planar top element are non-symmetrical about two axes in the plane of the planar top element.

4. The medical implant delivery system of claim 1, wherein the plurality of openings through the planar top element are the shape of a keyhole.

5. The medical implant delivery system of claim 1, wherein the plurality of openings through the planar top element include a multiple-component shape comprising:
a round opening component configured to receive at least a portion of a round medical implant; and
a rectangular opening component that intersects with the round opening component, the rectangular opening component having one side dimension that is less than the diameter of the round opening component, the rectangular opening component being configured to receive at least a portion of the holder.

6. The medical implant delivery system of claim 1, wherein the planar top element includes two or more non-symmetrically shaped openings configured to receive two or more respectively and matching non-symmetrically shaped holders to which medical implants are coupled, such that when the holders and medical implants are received in the openings through the planar top element, the holders are aligned in predetermined orientations relative to the planar top element.

7. The medical implant delivery system of claim 6, wherein the respective predetermined orientations align the two or more non-symmetrically shaped holders in similar orientations.

8. The medical implant delivery system of claim 6, wherein the two or more non-symmetrically shaped openings include openings of different sizes configured to receive two or more respectively matching non-symmetrically shaped holders to which medical implants are coupled, wherein each non-symmetrically shaped holder to which a medical implant is coupled can only be received in one size of non-symmetrically shaped opening in the caddy.

9. The medical implant delivery system of claim 6, wherein the two or more non-symmetrically shaped openings include openings of different shapes configured to receive two or more respectively matching non-symmetrically shaped holders to which medical implants are coupled, wherein each non-symmetrically shaped holder to which a medical implant is coupled can only be received in one shape of non-symmetrically shaped opening in the caddy.

10. The medical implant delivery system of claim 1, wherein the planar top element includes two or more non-symmetrically shaped openings configured to receive two or more respectively matching non-symmetrically shaped holders to which medical implants are coupled, such that when the holders and medical implants are received in the openings through the planar top element, the holders are positioned at predetermined locations in the caddy.

11. The medical implant delivery system of claim 10, wherein the two or more non-symmetrically shaped openings include openings of different sizes configured to receive two or more respectively matching non-symmetrically shaped holders to which medical implants are coupled, and wherein the openings of different sizes correlate with medical implants of different sizes.

12. The medical implant delivery system of claim 10, wherein the two or more non-symmetrically shaped openings include openings of different shapes configured to receive two or more respectively matching non-symmetrically shaped holders to which medical implants are coupled, and wherein the openings of different shapes correlate with medical implants of different sizes.

13. The medical implant delivery system of claim 10, wherein the two or more non-symmetrically shaped openings include openings of different sizes configured to receive two or more respectively matching non-symmetrically shaped holders to which medical implants are coupled, and wherein the openings of different sizes correlate with medical implants of different types.

14. The medical implant delivery system of claim 10, wherein the two or more non-symmetrically shaped openings include openings of different shapes configured to receive two or more respectively matching non-symmetrically shaped holders to which medical implants are coupled, and wherein the openings of different shapes correlate with medical implants of different types.

15. The medical implant delivery system of claim 10, wherein the two or more non-symmetrically shaped openings include openings of different sizes configured to receive two or more respectively matching non-symmetrically shaped holders to which medical implants are coupled, wherein each non-symmetrically shaped holder to which a medical implant is coupled can only be received in one size of non-symmetrically shaped opening in the caddy.

16. The medical implant delivery system of claim 10, wherein the two or more non-symmetrically shaped openings include openings of different shapes configured to receive two or more respectively matching non-symmetrically shaped holders to which medical implants are coupled, wherein each non-symmetrically shaped holder to which a medical implant is coupled can only be received in one shape of non-symmetrically shaped opening in the caddy.

17. A medical implant delivery system, comprising:
a medical implant;
a holder coupled to the medical implant and having a first area and a second area, wherein the second area is at least in part perpendicular to the first area;
one or more markings on the first area that include basic identifying information associated with the medical implant; and
a caddy configured to receive the holder coupled to the medical implant, the caddy comprising:
  a planar top element having a top surface, a bottom surface, and an opening that extends through the planar top element from the top surface to the bottom surface, and
  a support structure coupled to the planar top element on the bottom surface side such that the support structure provides a volume adjacent to the bottom surface configured to allow circulation of sterilization substances within the volume, and
  wherein the opening through the planar top element has a non-symmetrical shape about at least one primary axis of the planar top element, wherein the opening is configured to receive a matching non-symmetrically shaped holder to which a medical implant is coupled, such that when the holder and medical implant are received in the opening through the planar top element, the holder is aligned in a predetermined orientation relative to the planar top element.

18. The medical implant delivery system of claim 17, further comprising one or more markings on the second area that include identifying information associated with the medical implant that is of greater detail than the basic identifying information.

19. The medical implant delivery system of claim 17, wherein the caddy is configured to display the first area markings of the holder when the holder is received in the caddy.

20. The medical implant delivery system of claim 17, wherein the planar top element includes two or more types of non-symmetrically shaped openings of different types configured to receive two or more respectively matching non-symmetrically shaped holders to which medical implants are coupled, wherein each type of non-symmetrically shaped holder to which a medical implant is coupled can only be received in one type of non-symmetrically shaped opening in the caddy.

* * * * *